United States Patent
Dalmau

[19]

[11] Patent Number: 6,146,138
[45] Date of Patent: Nov. 14, 2000

[54] METHOD AND DEVICE FOR A NON-TRAUMATIC EXPANSION OF THE BONE FOR RECEIVING AFFIXING MEANS FOR DENTAL PROSTHETICS

[76] Inventor: Marcela Ridao Dalmau, Coma-Pedrosa, 8, Urb. Can Xicota, 08186 Llica d'Amunt, Spain

[21] Appl. No.: 09/238,301

[22] Filed: Jan. 28, 1999

[51] Int. Cl.⁷ .................................................. A61C 3/00
[52] U.S. Cl. ........................ 433/141; 433/165; 433/173
[58] Field of Search .................................. 433/102, 141, 433/165, 172, 173, 174, 175

[56] References Cited

U.S. PATENT DOCUMENTS

| | | | |
|---|---|---|---|
| 4,190,958 | 3/1980 | Martin et al. | 433/102 |
| 4,334,865 | 6/1982 | Borle | 433/221 |
| 4,340,364 | 7/1982 | Deemer | 433/75 |
| 4,406,623 | 9/1983 | Grafelmann et al. | 433/174 |
| 4,746,294 | 5/1988 | Colombo et al. | 433/174 |
| 5,087,201 | 2/1992 | Mondani et al. | 433/174 |
| 5,205,745 | 4/1993 | Kamiya | 433/173 |
| 5,259,398 | 11/1993 | Vrespa | 128/898 |
| 5,302,129 | 4/1994 | Heath et al. | 433/224 |
| 5,312,255 | 5/1994 | Bauer | 433/174 |
| 5,503,554 | 4/1996 | Schoeffel | 433/102 |

*Primary Examiner*—John J. Wilson
*Attorney, Agent, or Firm*—Horst M. Kasper

[57] ABSTRACT

Non-traumatic expansion devices for the bone for receiving affixing means for dental prosthetics, each expansion device being formed by a one-piece component (1) having an upper base (11) formed as a prismatic screw head. A center body (3) has milled generating lines extending in axial direction. A first transition area (5) is disposed between the center body (3) and the upper base (11). A threaded end (9) has a shape of an elongated cone and a second transition area (7) has a conical shape tapering toward the threaded end (9). Each expansion device has a different thickness and length on the threaded end (9) depending on the type of required expansion. The expansion device has the function of a screw for the purposes of drilling the bone and keeping the bone mass whole.

6 Claims, 1 Drawing Sheet

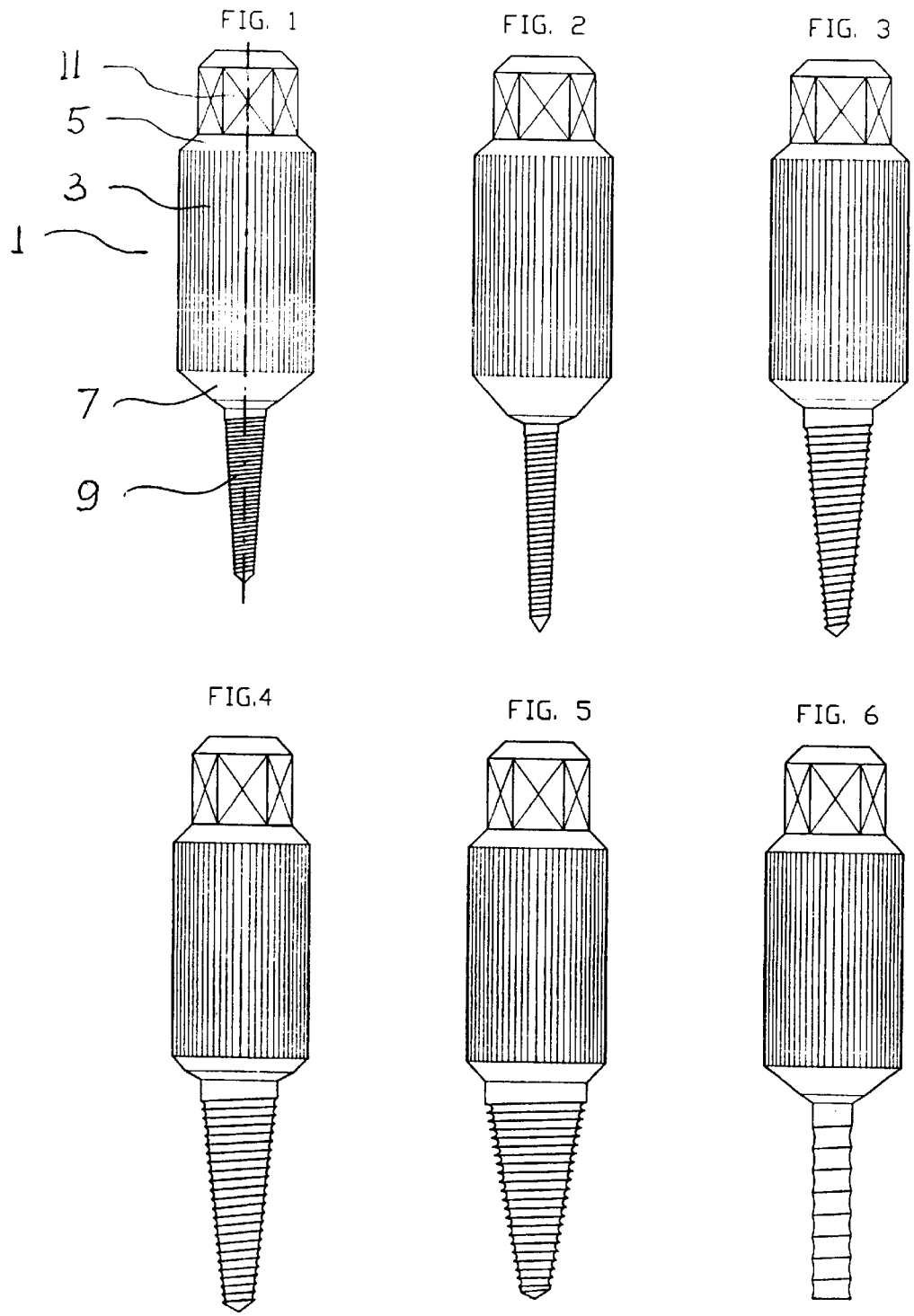

METHOD AND DEVICE FOR A NON-TRAUMATIC EXPANSION OF THE BONE FOR RECEIVING AFFIXING MEANS FOR DENTAL PROSTHETICS

BACKGROUND OF THE INVENTION

1. Field of the Invention

The present invention relates to a method and to a device for a non-traumatic expansion of a bone for receiving fastening and affixing means for dental prosthetics.

2. Brief Description of the Background of the Invention Including Prior Art

The affixing techniques and methods of dental prosthetics consist essentially in the use of the state of the art and methods for integrating and implanting dental replacement elements into the maxillaries. At the present time, the use of these techniques is accepted within a broad field of applications depending on the different techniques or systems to be employed.

Basically, the present known means and devices to perform and carry out a prosthetic implant of a dental configuration, are based to a large degree on the use of osteotomes.

These osteotomes are of the kind of a chisel which perform a required and adequate bone expansion for the placing of an implant, wherein the contact tip of the osteotome is placed on the dental base and the osteotome is introduced into the dental base by tapping the top of the osteotome with a mallet or small hammer and, as the introduction of the osteotome progresses, there results a bone expansion.

The above described technique is the most widely employed method and system at this time for the bone expansion for the placement dental implants. However, this technique is also a traumatic technique and method and, consequently, is accompanied by the disadvantages of this type of technique and method.

Among the most important disadvantages or inconveniences associated with the use of this method are:

Damage to the bone, up to and including breaking and chipping of the bone, as a result of tension created at the dental base with each tap of the mallet or small hammer onto the osteotome. In some instances, a complete deterioration of the dental base can occur, and this deterioration of the dental base requires extensive repairs.

Difficulty in the osteointegration and difficulty in the cohesion based on an incomplete contact between the elements, i.e. the osteotome and bone.

Alignment defect of the fixation axis because the bone expansion can neither be controlled nor adjusted.

Because of these inconveniences, there exists a demand for the development of new means which will reduce the problems associated with the current traumatic techniques and methods.

This type of demand does not only have economical implications in regard to the adoption and development of new techniques, but the evident social connotations in these fields are also to be considered.

A study and development of a device for the expansion of the bone is taught by Wolf and is referred to in the field as the Wolf principle. This principle establishes that the bone is being reshaped as a function of the forces applied to it. Therefore, the bone is a mass which can be expanded, depending on the stimulus required to maintain its form and density.

Numerous techniques are in fact known to obtain a bone expansion or bone enlargement, such as:

grafting onlays sub-central graftings of the maxillary cavities graftings related to bone regeneration techniques.

Enlargement methods of atrophic crests with chisels to provoke "stem fractures" and thereby to widen the bone width have been described.

Hilt Tatan started working in the field of bone expansion and the development of some techniques in the late eighties. Subsequently, it was Dr. Summers who designed cylindrical-conical-shaped instruments which were employed as expansion devices and it was Dr. Summers who called these devices osteotomes.

The present invention is developed with the purpose of overcoming these difficulties and it is planned as an innovative alternative and with advantages for prosthetic implant operations and processes which require a bone expansion in the dental base.

SUMMARY OF THE INVENTION

1. Purposes of the Invention

It is an object of the present invention to provide for the use of a series of expansion devices which minimize the surgical trauma as compared to the use of the osteotomes that are currently being used in dental implants.

It is an object of the present invention to provide for an improved device for non-traumatic bone-expansion devices for the implanting and affixing of dental prosthetic devices.

It is another object of the present invention to provide an advantageous and innovative alternative for dental implants that have the need of bone expansion in the base.

These and other objects and advantages of the present invention will become evident from the description which follows.

2. Brief Description of the Invention

The present invention provides for a non-traumatic expansion device for the bone for dental prosthetic implants. A one-piece expansion device is formed of an upper base, shaped as a prismatic screw head, and a center body having milled generating lines extending in an axial direction. A first transition area is disposed between the center body and the upper base. The first transition area has a conical shape tapered toward the upper base. A threaded end has a shape of an elongated cone. A second transition area is disposed between the center body and the threaded end. The second transition area has a conical shape tapered toward the threaded end.

The threaded end can have a shape of an elongated cone, and the thickness of the threaded end is preferably dependent on the type of expansion required.

The threaded end has a shape of an elongated cone, and the thickness of the threaded end is uniform throughout the longitudinal extension of the threaded end.

In addition, the present invention provides for a method for expanding a bone for receiving a dental prosthetic implant. A build-up of the maxillary and mandible bone, respectively, is designed. There is performed a drilling into a bone crest of the maxillary and mandible bone respectively, employing the one-piece expansion device. The expansion device is screwed up to a desired depth into the bone crest preferably expanding the bone and an implant is placed into the upper base of the expansion device. The gum tissue surrounding the implant is sutured and closed to complete the process.

The non-traumatic bone-expansion devices according to the present invention establish a substantial innovation over the original bone expansion devices of Dr. Summers. The size, the design and the method of use have been modified in that the non-traumatic bone expansion devices according to the present invention have the function of a screw, keeping the bone mass whole.

Differences between distinct bone types:

According to the thesis of Dr. Carl Misch, the available bone divisions can be classified in four sub-groups:

| Type A: | bone width | more than | 5 mm |
| --- | --- | --- | --- |
| | bone height | more than | 10–12 mm |
| | bone length | more than | 5 mm |
| | bone angle | less than | 30 % |

Therapeutic option to be applied in this case is an implant in the form of a root.

| Type B: | bone width | | 2.5–5 mm |
| --- | --- | --- | --- |
| | bone height | more than | 10–12 mm |
| | bone length | more than | 15 mm |
| | bone angle | less than | 20 % |

Therapeutic option to be applied:
1. Osteoplasty
2. Enlargement for esthetic requirements
3. Narrow implants in lamina form or having a diameter of 3.3 mm Type C: Bone having an unfavorable height and width, as well as length and angle Type D: Bone characterized by:
  Severe atrophy
  Basal bone loss
  Plane upper maxillary
  Severe bone resorption Therapeutic option to be applied:
  Enlargement
  Endosteum implants
  Subperiostic implants The implant classification set forth by Misch is based on four types of partial missing teeth included in the Kennedy-Applegate system. This facilitates the contacts between the great number of dentists who already know this classification, and allows the use of the therapeutic methods and common principles established for each class.

Class I:
Patients having movable anterior teeth. Good bone height, width, and depth.

Class II:
Patients who lost teeth in the posterior segment. Sufficient bone available.

Class III:
A patient of class III who is a candidate for implants has a large gap in the posterior section or has lost only one anterior tooth.

Class IV:
The patient of class IV has a toothless gap between teeth in the anterior section at the central line. Frequently, the anterior bone is insufficient and the insertion of bone graftings before proceeding to the direct insertion of the implants is common.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

In the accompanying drawings, in which are shown several of the various possible embodiments of the present invention:

FIG. 1 is a first embodiment of an expansion device;

FIG. 2 is a second embodiment of an expansion device;

FIG. 3 is a third embodiment of an expansion device;

FIG. 4 is a fourth embodiment of an expansion device;

FIG. 5 is a fifth embodiment of an expansion device;

FIG. 6 is a sixth embodiment of an expansion device.

DESCRIPTION OF INVENTION AND PREFERRED EMBODIMENT

Each expansion device is formed by a one-piece component 1 having an upper base 11, a center body 3, and a threaded end 9.

According to FIGS. 1–6, the center body 3 includes milled generating lines extending in axial direction of the center body 3. The upper base 11 is formed in the shape of a prismatic screw head. A transition between the center body 3 and the upper base head 11 is provided by a conical section 5. A transition between the center body 3 and the threaded end 9 is provided by a second conical section 7.

The upper base 11 can have a diameter of from about 0.6 to 0.9 times the diameter of the center body 3, and preferably of 0.7 to 0.8 times the diameter of the center body 3.

The length of the center body 3 in axial direction is from about 1.5 to 6.0 times larger than the length of the upper base 11, and preferably of 2.5 to 4.0 times the length of the upper base 11.

The diameter of the center body 3 can be from 4 to 8 mm, and preferably 6 mm.

The size and shape of the tapered, threaded end 9 depends on the type of surgical procedure required.

The threaded end 9 according to FIG. 1 can for example have an axial length of from 7 to 14 mm and preferably an axial length of 10 mm. The threaded end 9 at the beginning can have a diameter of from 1 mm to 2.30 mm.

The threaded end 9 according to FIG. 2 can for example have an axial length of from 8 to 15 mm and preferably an axial length of 12 mm. The threaded end 9 at the beginning can have a diameter of from 1.5 mm to 3.0 mm.

The threaded end 9 according to FIG. 3 can for example have an axial length of from 8 to 15 mm and preferably an axial length of 12 mm. The threaded end 9 at the beginning can have a diameter of from 2.9 to 3.0 mm, for placing an implant having a diameter of from 3.0 to 3.30 mm.

The threaded end 9 according to FIG. 4 can for example have an axial length of from 8 to 15 mm and preferably an axial length of 12 mm. The threaded end 9 at the beginning can have a diameter of from 3.3 to 4.5 mm, for placing an implant having a diameter of from 3.8 to 4.2 mm.

The threaded end 9 according to FIG. 5 can for example have an axial length of from 8 to 15 mm and preferably an axial length of 12 mm. The threaded end 9 at the beginning can have a diameter of from 4.4 mm to 5.2 mm for placing an implant having a diameter of 5.0 mm.

The threaded end 9 according to FIG. 6 can for example have an axial length of from 8 to 15 mm and preferably an axial length of 12 mm. The threaded end 9 at the beginning has a diameter of 3.5 mm for an atraumatic build-up of a bone, where a receding bone line resulted from a loss of bone mass.

The use of the invention device serves for achieving a bone expansion by an progressive introduction of the threaded end 9 of the expansion device 1.

The difference in the expansion method according to the present invention as compared to the traumatic expansion performed with the use of osteotomes can be summarized in that the insertion and integration into the prosthetic base is performed with a dynamically fixed advance by feeding the threaded end 9 of the expansion device 1 such that the problems related to bone fractures by non-controlled stress during the tapping-in process of the osteotome during insertion are limited. In addition, the present invention provides for a secure and safe feed of the threaded end 9 by maintaining an axial feed direction during the implant phase.

The use of a chisel, as described above, is accompanied by the drawback that a slight misalignment of the head can cause a corresponding axial shifting.

The use of expansion devices according to the present invention makes the alignment easier to achieve based on the gradual and controlled feed advance.

Still another advantage of the present invention is that in cases of fine crest bone, the implant according to conventional methods causes normally a loss of bone mass, while, with the use of expansion devices according to the present invention, this loss of bone mass does not occur due to the above mentioned gradual and controlled feed advance.

Economically, the use of the expansion devices according to the present invention is comparable to the use of conventional devices and methods, and in specific cases, such as in cases of bones of classes II, III and IV, set forth above, the expansion device of the present invention is less expensive than the devices known in the art because the use of milling cutters and drills to finish the implant is not necessary.

The insertion and introduction of the expansion device elements can easily be performed by using a dynamometric wrench to control the desired pressure, or with a regular, adapted wrench in simpler cases.

The six expansion devices which cover substantially all clinical cases are shown in the figures of the enclosed drawings. FIGS. 1–6 show the different thicknesses of the conical tips or threaded ends 9 and center body 3 of the expansion device 1, to be introduced into the bone, and the upper base 11 provided at the opposite end of each expansion device 1, which upper base 11 is formed at a nut, to facilitate the use of a corresponding wrench.

Normally, the expansion device shown FIG. 2 is in particular indicated for a fine and sharp bone when starting the perforation of the bone, and subsequently, once the initial perforation is performed, the expansion device with the appropriate thickness corresponding to the desired separation for the implant, is employed.

FIG. 6 shows an expansion device to be employed to dislodge the bone mass to the sides and to avoid bone loss, by compacting the bone around the implant.

The method and surgery technique for a bone expansion with the devices according to the present invention includes the following steps:

1. Design and build-up of the bone.

This step is the same as conventionally employed, bone of total thickness.

2. Drilling of the cortical of the bone crest.

A. In case of a bone of the type D and in case a peri-implant and no expansion is to be achieved, this step can be performed with a round drill or milling tool having a diameter of 1 mm.

B. If a bone expansion is to be achieved, several perforations will be made in the crest with a fissure drill or milling tool (tungsten), following a line of 4 mm and with the same drill or milling tool, the line will be united to form a furrow or rut.

3. Expansion of the bone.

A. Sequentially introducing the expansion device into the perforation in the bone crest up to the desired depth and thickness. The depth is measured in each expansion device and the thickness depends of the last expansion device used.

the expansion device of FIG. 1 is employed to initiate a first expansion;

the expansion device of FIG. 2 is employed to perform a second expansion;

the expansion device of FIG. 3 is employed for implants having a diameter of from 3 to 3.30 mm;

the expansion device of FIG. 4 is employed for implants having a diameter of from 3.8 to 4.20 mm;

the expansion device of FIG. 5 is employed for implants having a diameter of 5 mm;

the expansion device of FIG. 6 is employed for a non-traumatic built-up of a receding bone crest (cavity) caused by loss of bone mass.

B. In the center of the furrow or rut, the expansion will start like in the above-mentioned way; this furrow or rut will facilitate the expansion avoiding a fracturing of the bone wall.

4. Placement of Implant.

Placing the implants as a function of the thickness and length of the bed prepared, the preference being self-threading implants, however, impacted cylinders can also be used.

5. Suturing and closing.

It will be understood that each of the elements described above, or two or more together, may also find a useful application in other types of expansion devices differing from the types described above.

While the invention has been illustrated and described as embodied in the context of a method and a device for a non-traumatic expansion for the bone for receiving affixing means for dental prosthetics, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A non-traumatic expansion device for the bone for dental prosthetic implants, comprising a one-piece expansion device (1) formed of an upper base (11) formed as a prismatic screw head;

a center body (3) having milled generating lines extending in an axial direction;

a first transition area (5) disposed between the center body (3) and the upper base (11), wherein the first transition area has a conical shape tapering toward the upper base (11), a threaded end (9) having a shape of an elongated cone;

a second transition area (7) disposed between the center body (3) and the threaded end (9), wherein the second transition area (7) has a conical shape tapering toward the threaded end (9).

2. The non-traumatic expansion device according to claim 1, wherein the threaded end (9) has a shape of an elongated cone, and the thickness of the threaded end (9) is dependent on an expansion to be required.

3. The non-traumatic expansion device according to claim 1, wherein the threaded end (9) has a shape of an elongated cone, and the thickness of the threads is uniform throughout a longitudinal extension of the threaded end (9).

4. A non-traumatic expansive device for the bone for dental prosthetic implants comprising:

a piece showing a center portion of a cylindrical shape with a surface of milled lines and having an upper end and having a lower end;

a first transition area attached to the upper end, wherein the first transition area has a frustro-conical shape tapering upwardly to narrow to an upper side;

an upper part finished in a shape of a prismatic screw head and attached to the upper side of the frustro-conical shape;

a threaded end having a shape of an elongated cone and attached to the lower end.

5. The non-traumatic expansion device for the bone for dental prosthetic implants, according to claim 4 further comprising a second piece showing a center portion of a cylindrical shape with a surface of milled lines and having a second upper end and having a second lower end;

a second upper part finished in a shape of a prismatic screw head and attached to the second upper end;

a second threaded end not having a conical shape and attached to the second lower end to be used to push the bone mass to its sides avoiding the loss of bone and comprising the same (bone) around the implant.

6. A method for expanding a bone for receiving a dental prosthetic implant, comprising the steps designing a build-up of the maxillary and mandible bone, respectively;

drilling into a bone crest of the maxillary and mandible bone, respectively employing a one-piece expansion device (1) formed of an upper base (11) formed as a prismatic screw head, a center body (3) having milled generating lines extending in an axial direction, a first transition area (5) disposed between the center body (3) and the upper base (11), wherein the first transition area has a conical shape tapering toward the upper base (11), a threaded end (9) having a shape of an elongated cone, a second transition area (7) disposed between the center body (3) and the threaded end (9), wherein the second transition area (7) has a conical shape tapering toward the threaded end (9);

screwing the expansion device up to a desired depth into the bone crest thereby expanding the bone;

removing the expansion device from the bone crest and leaving an expanded hole;

placing an implant into the expanded hole;

suturing and closing of gum tissue surrounding the implant.

* * * * *